US010149792B2

(12) United States Patent
Drake et al.

(10) Patent No.: US 10,149,792 B2
(45) Date of Patent: *Dec. 11, 2018

(54) COUNTERTRACTION SURGICAL ASSEMBLY

(71) Applicant: Allen Medical Systems, Inc., Batesville, IN (US)

(72) Inventors: Jesse S. Drake, Westborough, MA (US); Dustin T. Libby, Naples, FL (US)

(73) Assignee: Allen Medical Systems, Inc., Batesville, IN (US)

( * ) Notice: Subject to any disclaimer, the term of this patent is extended or adjusted under 35 U.S.C. 154(b) by 166 days.

This patent is subject to a terminal disclaimer.

(21) Appl. No.: 14/632,376

(22) Filed: Feb. 26, 2015

(65) Prior Publication Data

US 2015/0164724 A1    Jun. 18, 2015

Related U.S. Application Data

(63) Continuation of application No. 13/250,381, filed on Sep. 30, 2011, now Pat. No. 8,997,749.

(51) Int. Cl.
*A61G 13/00* (2006.01)
*A61F 5/00* (2006.01)
(Continued)

(52) U.S. Cl.
CPC .......... *A61G 13/0036* (2013.01); *A61F 5/04* (2013.01); *A61G 13/0081* (2016.11); *A61G 13/123* (2013.01); *A61G 13/1285* (2013.01)

(58) Field of Classification Search
CPC .......... A61B 6/00; A61B 6/04; A61B 6/0407; A61G 7/00; A61G 7/05; A61G 7/0503;
(Continued)

(56) References Cited

U.S. PATENT DOCUMENTS 3,675,944 A * 7/1972 Kobayashi ............. B62K 15/00
                                                 280/278
4,268,055 A *  5/1981 Bell ......................... B62K 3/10
                                                 280/278

(Continued)

OTHER PUBLICATIONS

EP Search Report for Application 12186260.1; dated Apr. 5, 2013; Place of Search—The Hague; Date of Completion of the Search—Mar. 27, 2013.

*Primary Examiner* — Kari Rodriquez
(74) *Attorney, Agent, or Firm* — Kenneth C. Baran

(57) ABSTRACT

A surgical assembly (20) comprises a post (100) having a longitudinally extending axis (104), a support (56) for resisting movement of the post in a negative longitudinal direction, and a platform (70) offset from the support in a positive longitudinal direction. The platform includes an opening (82) through which the post projects. The opening includes a throat (86). The post has a first dimension which renders the post incapable of passing through the throat and a second dimension which renders the post capable of passing through the throat. Alternate embodiments in which the post can be removably engaged with the support and platform and disengaged therefrom without translating the post in the longitudinal direction are also disclosed.

18 Claims, 10 Drawing Sheets

(51) Int. Cl.
*A61G 13/12* (2006.01)
*A61F 5/04* (2006.01)

(58) Field of Classification Search
CPC ............... A61G 7/0506; A61G 7/0507; A61G 2007/0508; A61G 2007/0509; A61G 2007/0518; A61G 7/065; A61G 7/075; A61G 7/0755; A61G 13/00; A61G 13/036; Y10T 403/39; Y10T 403/3933; Y10T 403/3946; Y10T 403/3953; Y10T 403/3966; Y10T 403/3981; Y10T 403/33; Y10T 403/335; Y10T 403/3993
USPC .... 5/162, 280, 621, 622, 624, 630; 128/845, 128/846, 869, 870; 602/32, 33, 35, 36, 602/39, 40; 606/237, 240, 241; 248/507, 248/549, 649; 70/361, 141; 403/101
See application file for complete search history.

(56) References Cited

U.S. PATENT DOCUMENTS

| | | |
|---|---|---|
| 4,653,482 A | 3/1987 | Kurland |
| 5,515,562 A | 5/1996 | Miller et al. |
| 5,658,315 A | 8/1997 | Lamb et al. |
| 7,947,006 B2 | 5/2011 | Torrie et al. |
| 8,683,631 B2 | 4/2014 | Bellows et al. |
| 2011/0023893 A1 | 2/2011 | Striggow et al. |

\* cited by examiner

COUNTERTRACTION SURGICAL ASSEMBLY

TECHNICAL FIELD

The subject matter described herein relates to a surgical assembly and particularly to a quick release surgical post and related structural elements. One example application for the assembly is as a perineal post for applying countertraction during procedures such as fracture repair, hip arthroscopy and hip replacement surgery.

BACKGROUND

Surgeons performing certain surgical procedures find it necessary to apply traction and countertraction to the surgical patient. For some lower extremity procedures the surgeon uses a vertically extending perineal post in the patient's perineal region to apply appropriate countertraction. The post is typically mounted on the surgical table at a post/table interface and is covered with a cylindrical pad. Intraoperative removal of the post can be problematic because the post/table interface is in a confined space under the sterile field. In addition at least the initial phase of post removal requires movement of the post in a direction parallel to its axis. This direction of motion is resisted by contact with the patient's groin and thigh tissue.

SUMMARY

One embodiment of a surgical assembly as described herein comprises a post having a longitudinally extending axis, a support for resisting movement of the post in a negative longitudinal direction, and a platform offset from the support in a positive longitudinal direction. The platform includes an opening through which the post projects. The opening includes a throat. The post has a first dimension which renders the post incapable of passing through the throat and a second dimension which renders the post capable of passing through the throat.

BRIEF DESCRIPTION OF THE DRAWINGS

The foregoing and other features of the various embodiments of the surgical assembly described herein will become more apparent from the following detailed description and the accompanying drawings in which.

DESCRIPTION

Figure 1:
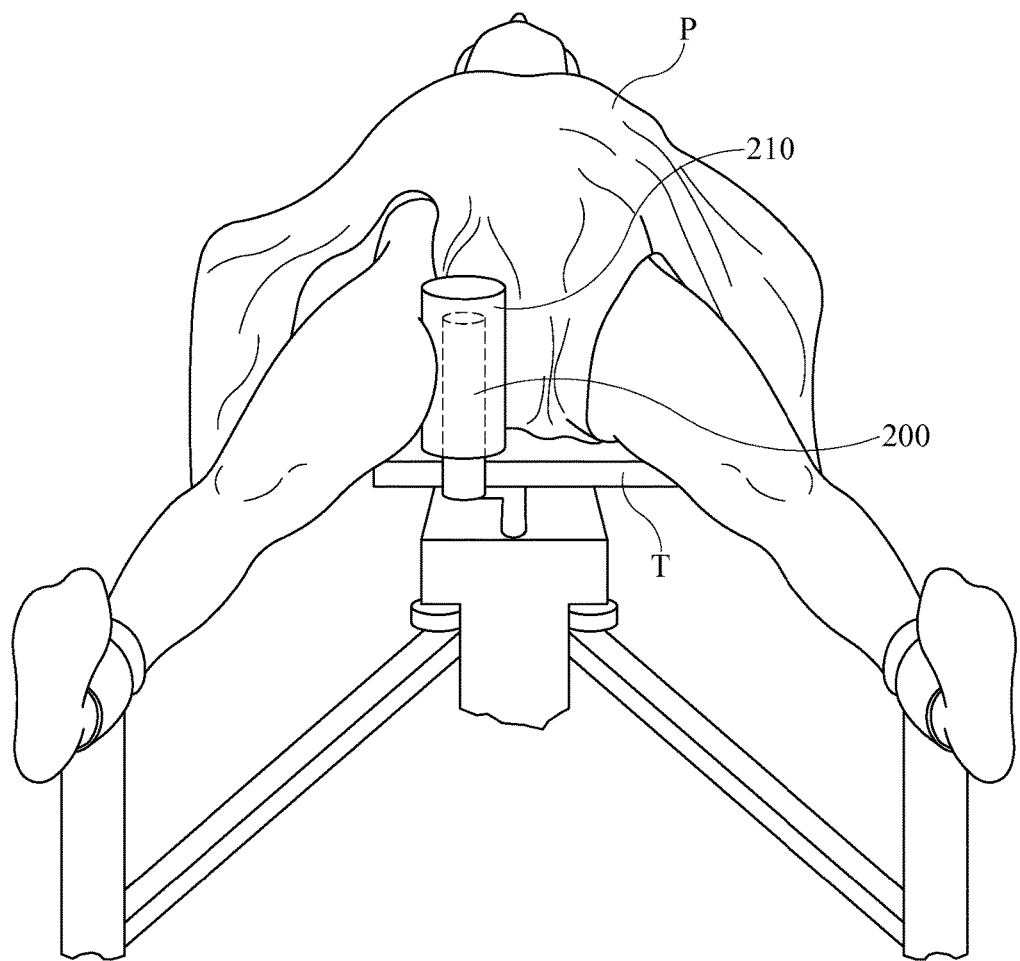
FIG. 1 is a view showing a supine patient on an operating table and a generically depicted perineal post extending vertically from the table so that the patient's inner thigh in the vicinity of his perineum bears against a pad installed on the post.

FIG. 1 shows a generically depicted perineal post assembly in the context of a supine patient P lying on an operating table T. The assembly includes a perineal post 200 extending vertically from the table, and a pad 210 mounted on the post.

FIGS. 2-5 show a surgical assembly, specifically a countertraction assembly 20, and three mutually orthogonal reference axes: a longitudinal axis 22, a lateral axis 24, and a transverse axis 26. The axes illustrated in the drawings each extend in respective positive directions from origin O. Left and right lateral directions are indicated by directional arrows L and R and correspond to the positive and negative lateral directions respectively.

Countertraction assembly 20 includes a laterally extending beam 32, left and right attachment brackets 34, and left and right handles 36. A surgical table extender includes rail adaptors 40, only the left one of which is shown, to permit equipment and accessories to be attached to rails extending along the sides of the table. A hook 42 is removably attached to each rail adaptor with a threaded connector having a knob 44 and a threaded shank (not visible). Each bracket 34 engages a hook 42 to cantilever mount the countertraction assembly on the surgical table.

An assembly substructure includes a truss 50 connected to the beam. The truss has an upper leg 52 and a lower leg 54. The substructure also includes a support or yoke 56 connected to the lower leg and having left and right feet 60. A locator 62, which is at least partly frustoconical, projects from each foot in the positive longitudinal direction.

The counteraction assembly also includes a platform 70 offset from support 56 in the positive longitudinal direction and secured by screws 72 to beam 32 and to upper leg 52 of truss 50. The platform has a substantially planar upper surface 74, a substantially planar lower surface 76, and a thickness t. The planes of the upper and lower surfaces define an interplanar envelope 80 also having a thickness t. The platform includes left and right platform openings 82 each having a circular portion 84 with a first diameter D1 and a throat portion 86 extending from the circular portion to an edge 88 of the platform. The throat has a minimum lateral width W in the interplanar envelope such that W is smaller than D1.

Figure 5:
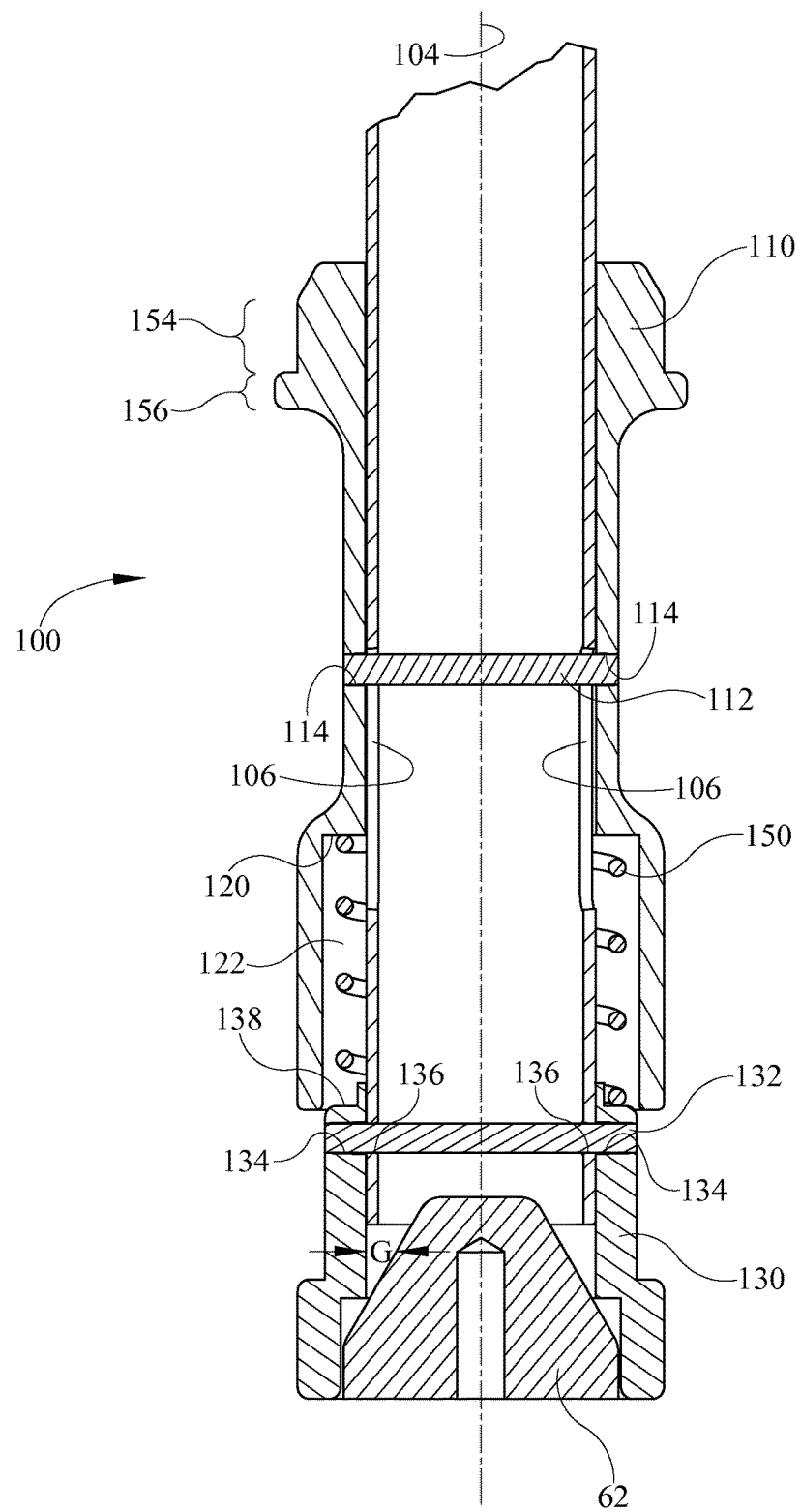
FIG. 5 is a sectioned elevation view of selected portions of the assembly showing the sleeve in a neutral position.

The countertraction assembly also includes a post 100 comprising a pole 102 having an axis 104 (seen best in FIGS. 5 and 6) and a pair of diametrically opposed slots 106 (visible in FIG. 5). The pole has a circular cross section whose diameter is, at most, no greater than throat width W and, in practice, is small enough to pass through the throat in the transverse direction. The post also includes a retainer illustrated as a sleeve 110 that circumscribes the pole. A sleeve dowel 112 extends through holes 114 in the sleeve and through slots 106 in the pole. Dowel 112 is retained in holes 114 by friction fit and/or an adhesive. The presence of slots 106 enables the sleeve to translate longitudinally along the pole. The sleeve has a relatively large diameter portion that defines a shoulder 120 and that cooperates with pole 102 to define an annulus 122.

The illustrated post also includes a mount adaptor 130 secured to the pole by an adaptor dowel 132 that extends through holes 134 in the adaptor and corresponding holes 136 in the pole. Dowel 132 is retained in holes 134, 136 by friction fit and/or an adhesive. A ledge 138 on the adaptor defines the lower end of annulus 122. As seen best in FIG. 5 the locator is received by the post, specifically by the mount adaptor in the illustrated embodiment, to locate or position the post spatially and to provide some resistance to movement of the post in the lateral and transverse directions. The support resists movement of the post in the negative longitudinal direction.

A coil spring 150, resides in annulus 122 radially intermediate the sleeve and the pole. The spring extends longitudinally from adaptor ledge 138 to shoulder 120.

Figure 2:
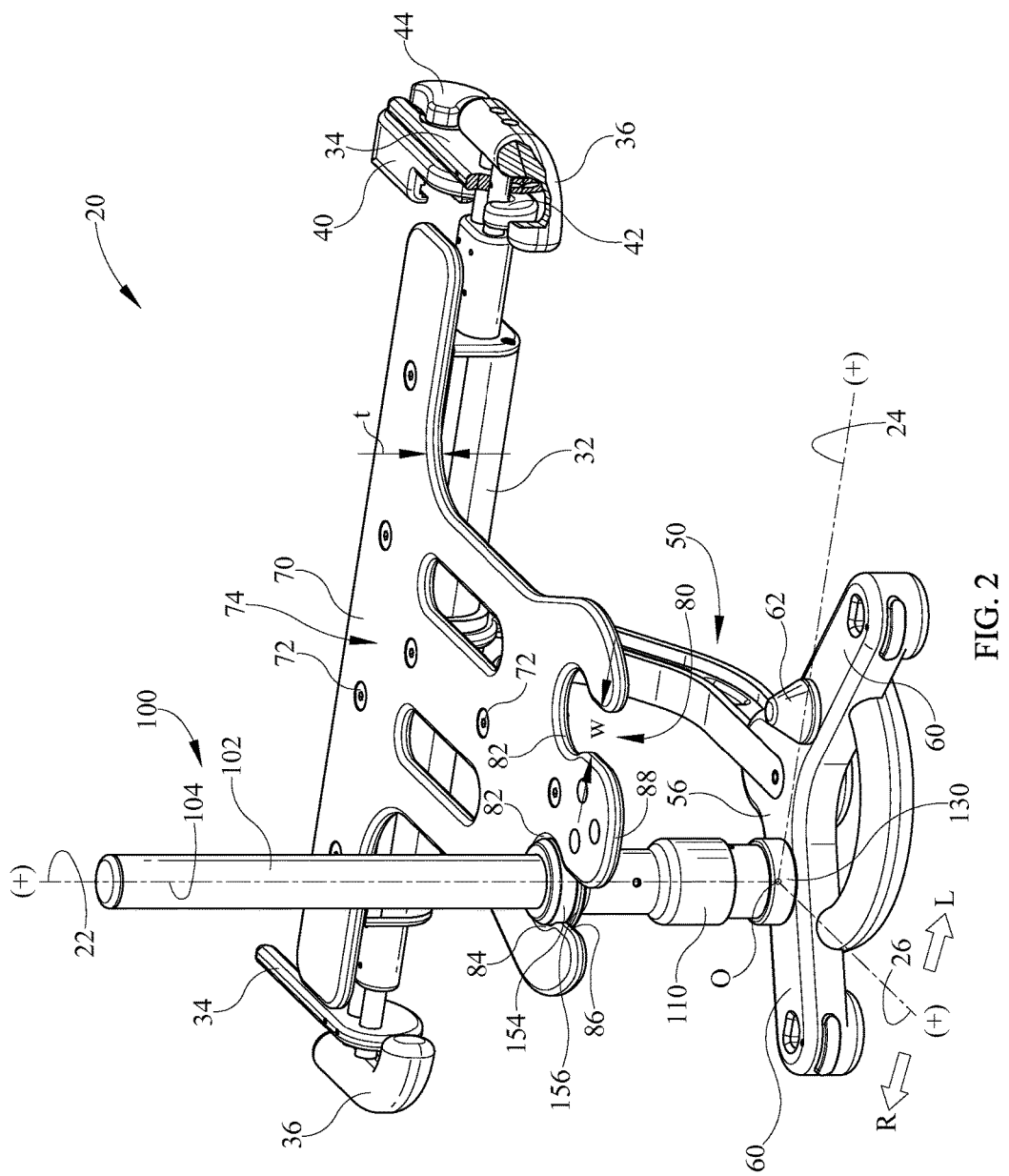
FIG. 2 is a perspective view of a surgical assembly described herein, in particular a perineal post with a translatable sleeve and related structural elements as seen by an observer positioned above and to one side of the assembly and with the sleeve in a first position that secures the post in place.

FIG. 2 shows post 100 positioned on locator 62 with the pole projecting through circular portion 84 of opening 82. In FIG. 2 spring 150 is compressed and therefore biases the sleeve longitudinally to a first position in which a first portion 154 of the sleeve having a diameter larger than width W of the throat projects into interplanar envelope 80 within the circular portion 84 of opening 82, and in which a second, lip portion 156 of the sleeve contacts and bears against lower surface 76 of the platform. As a result, the post has a first dimension in the interplanar envelope large enough in relation to throat width W to render the post incapable of passing through the throat. The first dimension is the diameter of the sleeve first portion 154. Because of the force exerted by the spring, the first position is a default position. The assembly as seen in FIG. 2 is in a secured or locked state, i.e. the locator is received in the post and the sleeve is snugly confined by circular portion 84 of opening 82 such that the post cannot be easily moved out of position. In this state the assembly can be used to apply countertraction to a patient during surgery.

Figure 3:
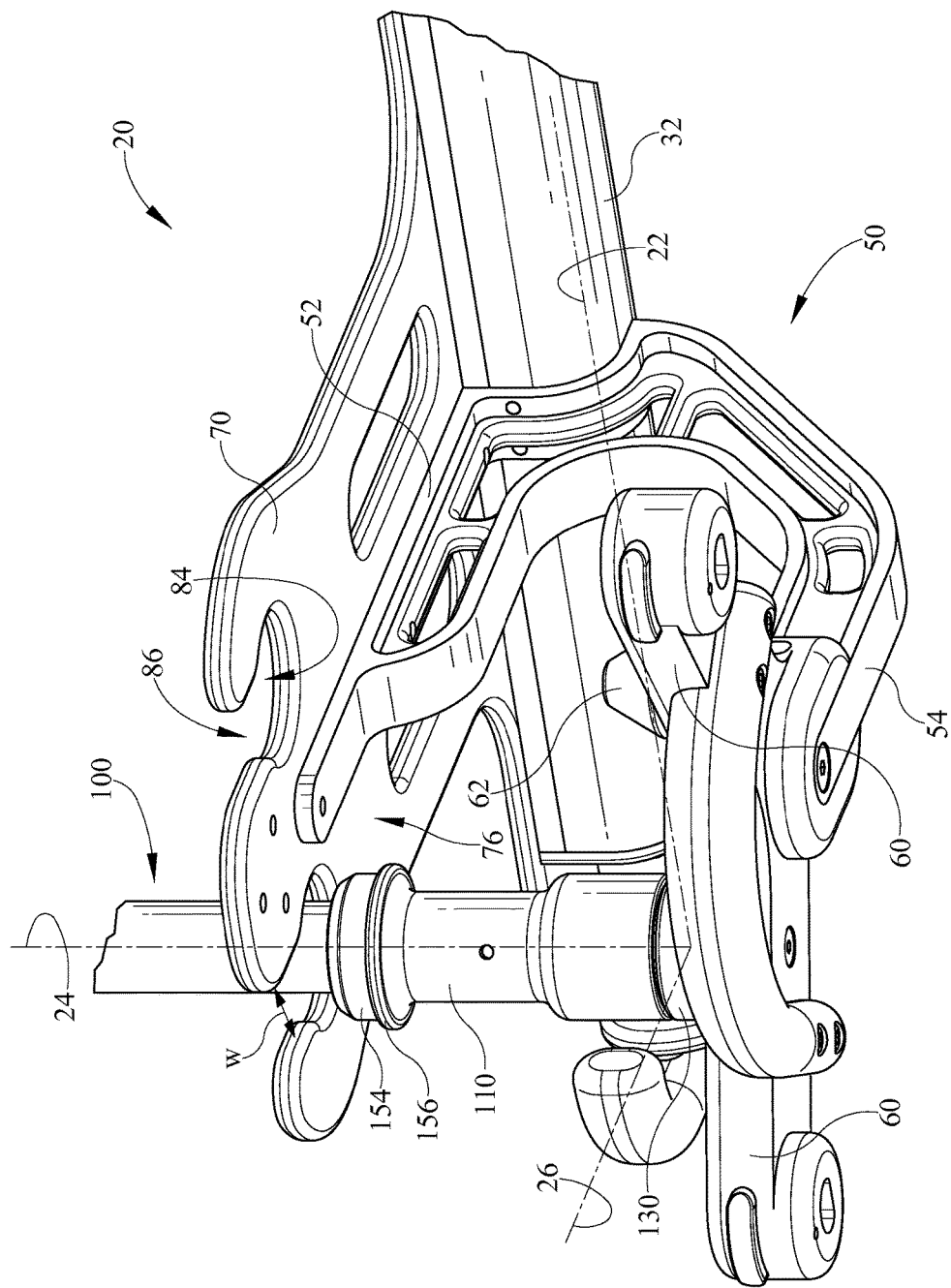
FIG. 3 is a view similar to that of FIG. 2 as seen by an observer positioned below the assembly and with the sleeve in a second position to facilitate the process of coupling the post to or removing the post from the related structural elements.
Figure 4:
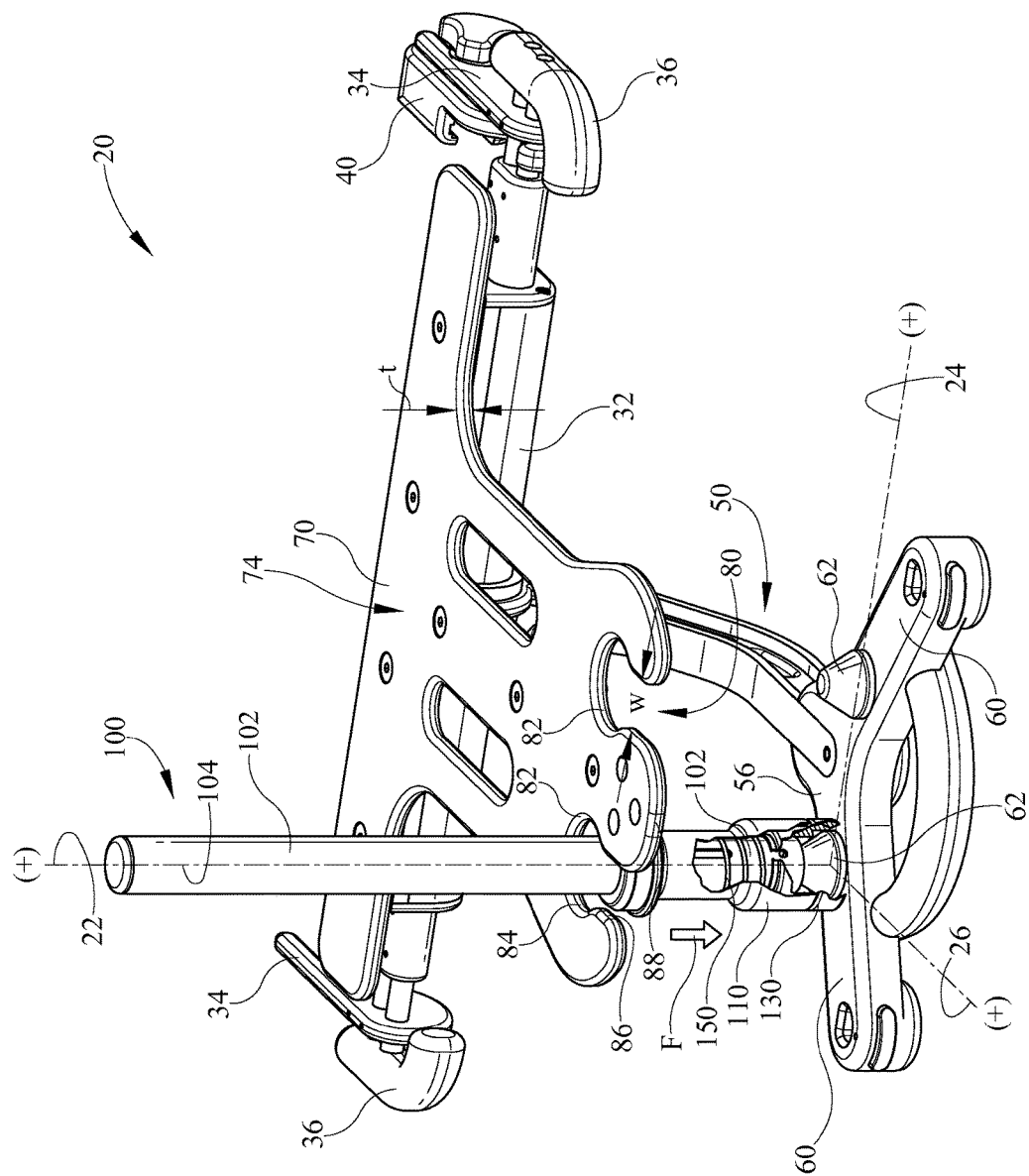
FIG. 4 is a view similar to that of FIG. 3 as seen by an observer positioned above the assembly.

FIGS. 3-4 show sleeve 110 having been translated to a second position by the application of a force F to further compress spring 150 thereby counteracting the biasing force that would otherwise urge the sleeve to the first position. The force is applied by an attendant who grasps the sleeve and pushes it in the negative longitudinal direction. In the second position, no portion of the sleeve having a diameter larger than width W of the throat projects into interplanar envelope 80. In practice the attendant would typically push the sleeve far enough that no portion of the sleeve projected into the interplanar envelope. As a result, the post has a second dimension in the interplanar envelope small enough in relation to throat width W to render the post capable of passing through the throat. The second dimension is the diameter of pole 102. As will become clear after describing FIG. 6, the second dimension of the illustrated embodiment would extend slightly above the plane of platform upper surface 74. The assembly as seen in FIGS. 3-4 is in a non-secured or unlocked state.

FIG. 5 shows the sleeve in a relaxed state, as it would be if the post were in place on the adaptor as in FIG. 2 but the platform were not present.

Figure 6:
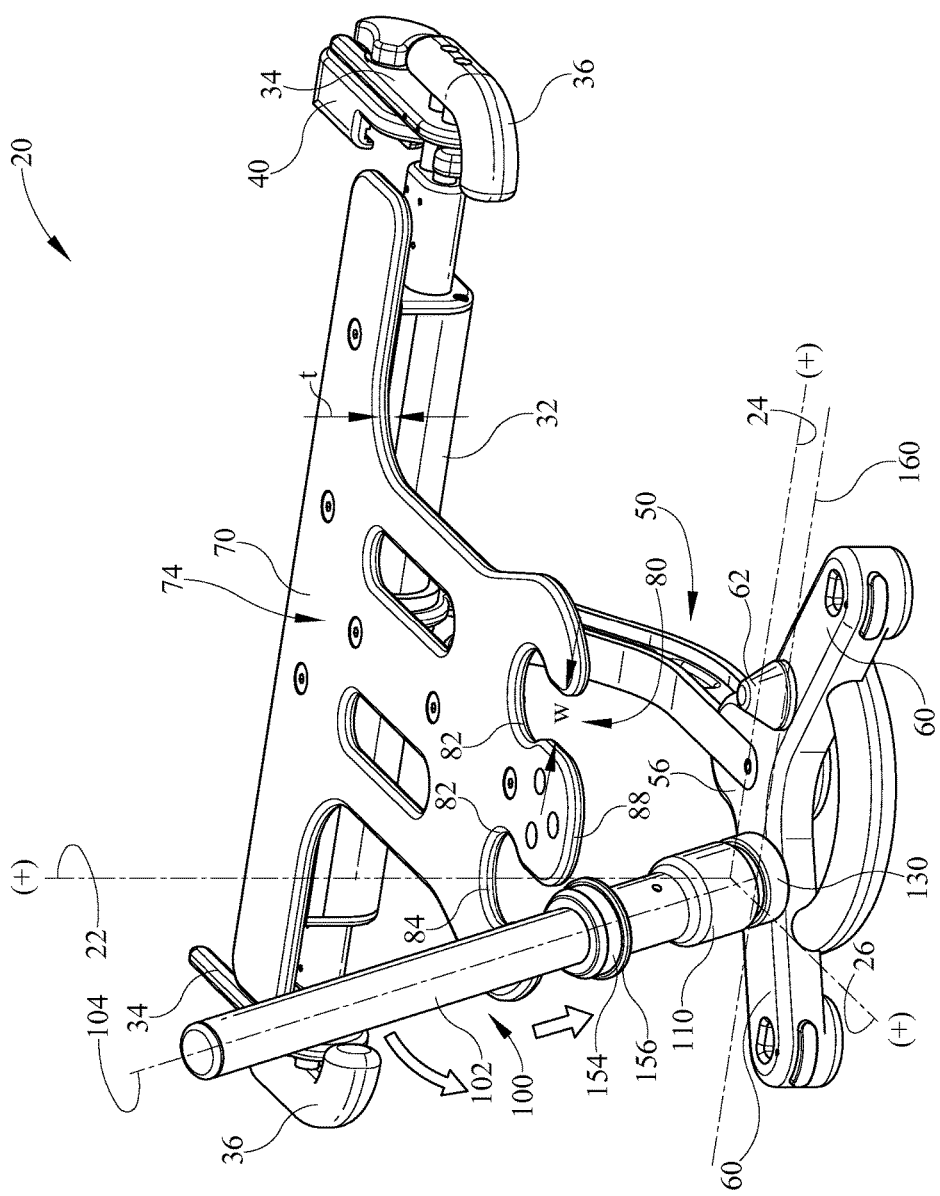
FIG. 6 is a view similar to that of FIGS. 2-4 showing the post having been rotated about a laterally extending axis to effect its removal.

FIG. 6 shows the post having been rotated about a laterally extending axis 160 to effect its removal. Clearance gap G (FIG. 5) between the frustoconical locator and the inside wall of the post enables the rotation. Locator geometries other than frustoconical can also be used provided only that the locator geometry will properly locate the post and will allow it to be rotated into position for installation and out of position for removal. As a result of the rotation, the portion of the post that passes through the throat includes a small segment of the post that, in the position of FIG. 2, is slightly above the plane of platform upper surface 74. Hence the earlier observation that the second dimension of the illustrated embodiment would extend slightly above the plane of platform upper surface 74. As seen in FIG. 6 the post can be engaged with and disengaged from the support and platform without any purposeful translation of the post longitudinally or in the direction of axis 104. In other words although a user might effect some incidental movement of the post longitudinally or in the direction of axis 104, such motion is not necessary to engage the post with the support and platform or to disengage it from the support and platform.

Figure 7:
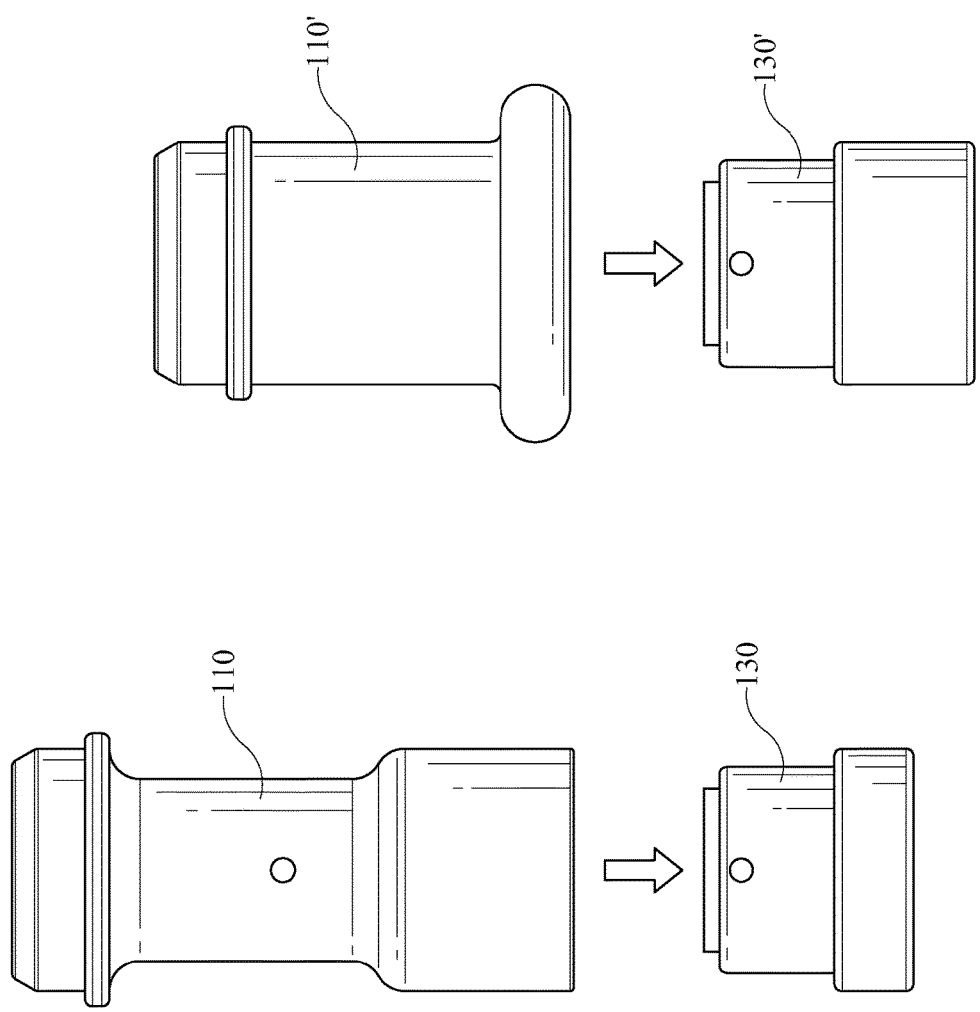
FIG. 7 is a side elevation view showing the sleeve and a mount adaptor of FIGS. 2-6 and also showing an alternate sleeve and mount adaptor.

FIG. 7 shows sleeve 110 and mount adaptor 130 as previously described and also shows a prototype sleeve 110' and adaptor 130'. The prototype sleeve is believed to be less ergonomic than sleeve 110 but is otherwise functionally and conceptually equivalent to sleeve 110.

The foregoing description describes removal of the post, however those skilled in the art will understand that installation of the post is merely the reverse of removal. The foregoing description is in the context of a post used on right foot 60 but also clearly applies to the left foot. In addition, although the foregoing description used a vertically extending perineal post as an example, the concepts and features disclosed and claimed herein can be used in other countertraction devices including those in which the post is oriented nonvertically.

Figure 8:
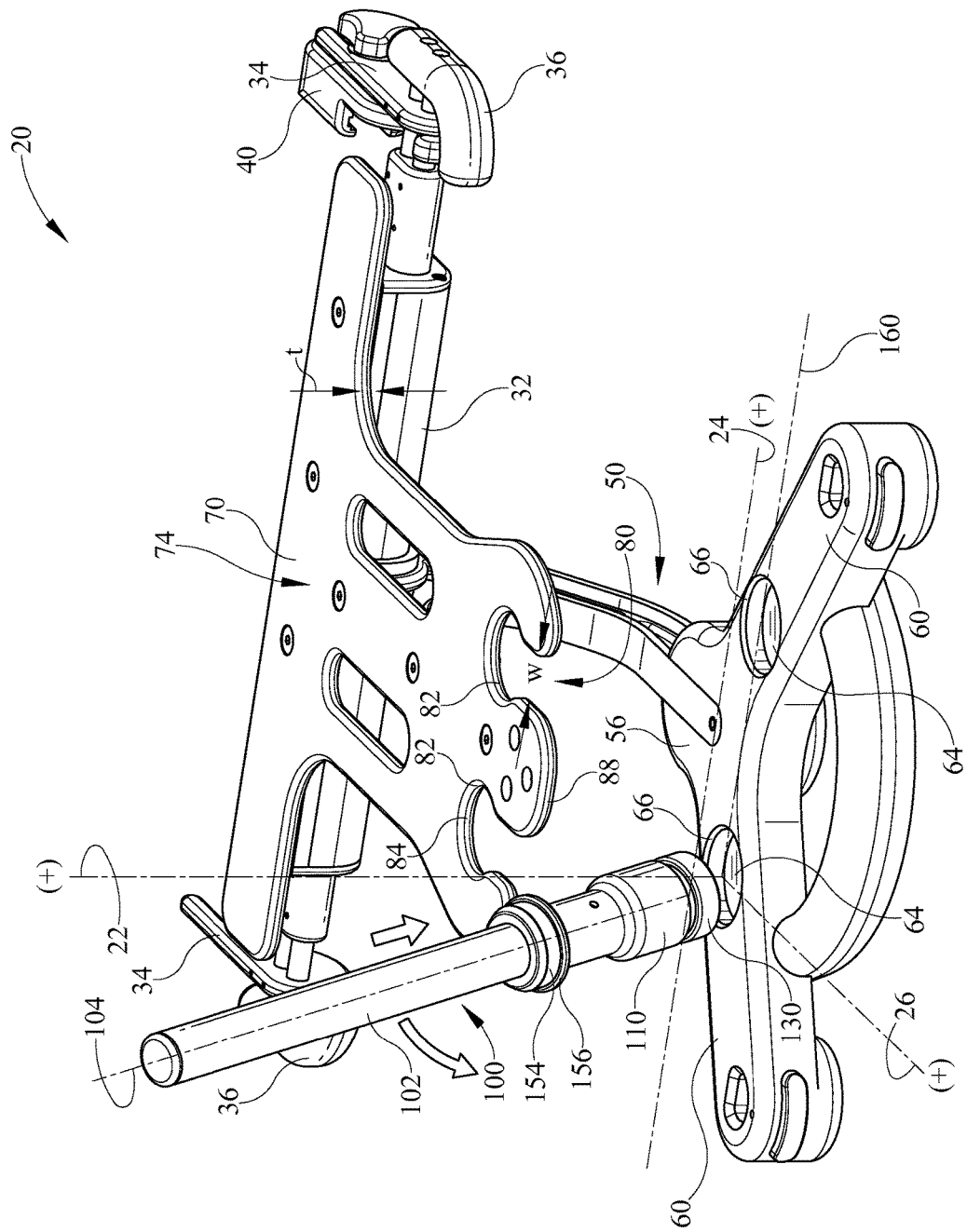
FIG. 8 is a view similar to that of FIG. 6 showing a variant of the countertraction assembly and showing the post having been removed

FIG. 8 is a view showing a variant of the countertraction assembly. In the illustrated variant each foot includes a counterbore 64 with a chamfer 66 in lieu of locator 62 seen in other embodiments. The diameter of the nonchamfered portion of the counterbore is slightly oversized relative to the diameter of the bottom of the post, for example by about 0.020 inches (approximately 0.5 mm). As a result the post fits snugly into the counterbore, but, due to chamfer 66 and the slight oversizing of the counterbore, can nevertheless be rotated about a laterally extending axis 160 to effect installation or removal. As with the embodiment of FIGS. 1-5, engagement of the post with the platform and support and disengagement of the post from the platform and support is carried out without the need for any purposeful translation of the post longitudinally or in the direction of axis 104. If the fit between the counterbore and post were too tight to permit rotation about axis 160, some small amount of purposeful translation of the post in the longitudinal direction (and in the direction of axis 104) would be necessary. However the required translation would be limited to the amount necessary for the bottom of the post to clear the top of the counterbore. It would not be necessary to translate the post in the longitudinal direction by an amount sufficient to cause the lower end of the post to pass longitudinally through platform opening 82.

Figure 9:
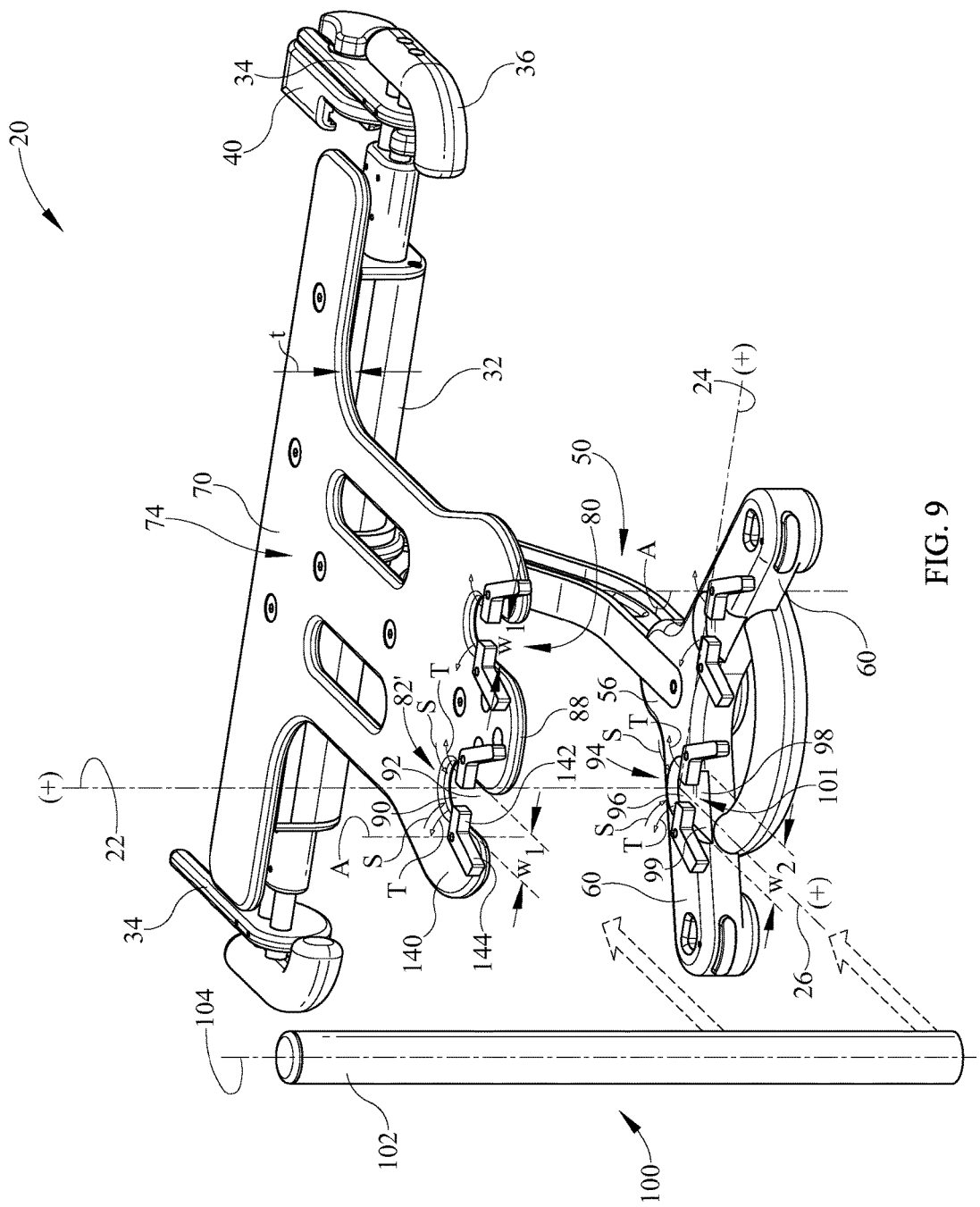
FIG. 9 is a view similar to that of FIG. 8 showing another variant of the countertraction assembly with the post having not yet been installed.

FIG. 9 is a view showing another variant of the countertraction assembly. In the embodiment of FIG. 9, the post has a circular cross section, and the sleeve 110 seen in other embodiments is absent. In addition, opening 82' has a semicircular portion 90, which conforms to the cross sectional geometry of the post, and a constant width portion 92 having a width W1. Width W1, the diameter of semicircular portion 90, and the diameter of post 102 are substantially equal to each other. Each foot 60 includes a recess 94 with a semicircular portion 96, which conforms to the cross sectional geometry of the post, and a constant width portion 98 having a width W2. The plane of the top of feet 60 and the plane of floor 99 of the recess bound a second interplanar envelope 101. Width W2, the diameter of semicircular portion 96, and the diameter of post 102 are substantially equal to each other. A locking element 140 having first and second wings 142, 144 is pivot mounted alongside one or both edges of the constant width portions 92, 98 of opening 82' and recess 94 respectively. Each locking element is rotatable about an axis A. Each locking element is spring loaded in rotational direction S to the position shown in the illustration in which first wing 142 of each element projects into the planform of the opening or recess either within or outside of respective interplanar envelopes 80, 101. A user installs the post by translating it in the transverse direction into the constant width portions of opening 82' and recess 94. Continued translation of the post toward semicircular portions 90, 96 causes the post to deflect the locking elements in rotational direction T, pushing the first wings aside so that the post can travel completely into the opening and recess. The deflection occurs without direct user intervention, i.e. without a user having to manipulate the elements independently of moving the post. Once the post has traveled past the locking elements, the elements spring back to their undeflected position. Because locking elements 140 cannot rotate any further in direction S than the position shown in the illustration, the first wing 142 of each element resists unintentional removal or accidental dislodgement of the post. In order to remove the post a user directly manipulates the lock by squeezing second wings 144 toward each other thus rotating the locking elements in direction T until first wings 142 no longer impede movement of the post in the direction of transverse axis 26. While holding the locking elements in this position the user independently moves the post out of the opening and recess in the transverse direction.

Other variants reflecting different combinations of projection 62, counterbore 64, constant width recess 94/locking element 140, constant width opening 82'/locking element 140 and non-constant width opening 82, used as appropriate at foot 60 and/or platform 70, may also provide satisfactory results. It is envisioned that projection 62, counterbore 64, and constant width recess 94/locking element 140 are the features best suited for use on feet 60 of support 56 and that constant width opening 82'/locking element 140 and non-constant width opening 82 are the features best suited for use on the platform.

Figure 10C:
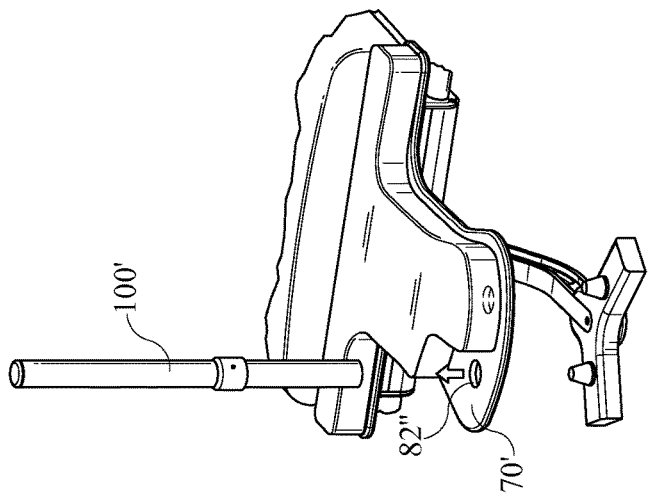
FIGS. 10A-10C are a sequence of views showing a prior art perineal post assembly with the post in its operative position, in an early phase of removal, and in a later phase of removal.
Figure 10B:
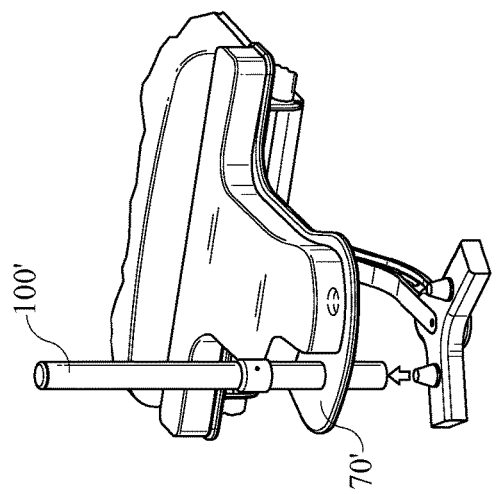
Figure 10A:
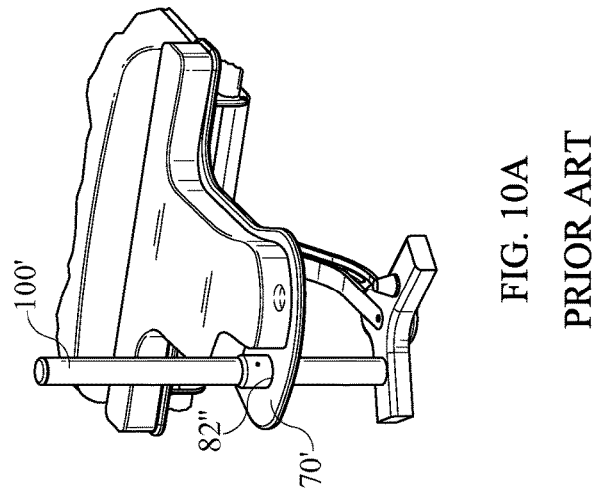

FIGS. 10A-10C are a sequence of views showing a pre-existing countertraction assembly. In FIG. 8A the post 100' extends through a simple opening 82' in platform 70'. As a result, removal of the post (FIGS. 8B-8C) involves a considerable movement of the post in the positive longitudinal direction which, as noted earlier in this application, can complicate intraoperative removal of the post.

Although this disclosure refers to specific embodiments, it will be understood by those skilled in the art that various changes in form and detail may be made without departing from the subject matter set forth in the accompanying claims.

What is claimed is:
1. A surgical assembly comprising:
   a post having a longitudinally extending axis, the post including a pole and a retainer;
   a support for resisting movement of the pole in a negative longitudinal direction;
   a locator projecting from the support in a positive longitudinal direction, the locator being receivable by the post, and the post being releasable from the locator by way of rotation of the post about a laterally extending axis;
   a platform offset from the support in the positive longitudinal direction, the platform having upper and lower surfaces defining an interplanar envelope and also having an opening which extends longitudinally through the platform, the opening comprised of a circular portion and a throat that extends horizontally from the circular portion to an edge of the platform;
   wherein the retainer is longitudinally positionable along the pole in:
      A) a first position in which the retainer projects into the interplanar envelope and is radially between the pole and the perimeter of the circular portion, and
      B) a second position in which the retainer does not project into the interplanar envelope.
2. The assembly of claim 1 wherein the post includes a mount adaptor and the locator is receivable by the mount adaptor.
3. The assembly of claim 1 wherein the locator has a geometry such that the post is releasable from the locator by way of a rotation about the laterally extending axis.
4. The assembly of claim 3 wherein the geometry is frustoconical.
5. The assembly of claim 1 wherein the locator and pole cooperate to define a radial gap therebetween.
6. The assembly of claim 1 wherein when the retainer is in the first position the dimension of the post longitudinally within the interplanar envelope is a first dimension that renders the post incapable of transiting horizontally through the throat and when the retainer is in the second position the dimension of the post longitudinally within the interplanar envelope is a second dimension that renders the post capable of transiting horizontally through the throat.
7. The assembly of claim 1 wherein the locator is a sub-element of the support.
8. A surgical assembly comprising:
   a post having a longitudinally extending axis, the post including a pole and a retainer;
   a support for resisting movement of the pole in a negative longitudinal direction;
   a platform offset from the support in a positive longitudinal direction, the platform having an opening comprised of a circular portion through which the post projects and a throat that extends from the circular portion to an edge of the platform;
   wherein the retainer circumscribes the pole and is slidably positionable along the pole to a first position in which the retainer occupies the circular portion of the opening and resists horizontal movement of the post into the throat portion of the opening and a second position in which the retainer does not resist horizontal movement of the post into the throat portion of the opening.
9. The assembly of claim 8 wherein:
   A) in the first position, a first portion of the retainer, which first portion has a diameter larger than the width of the throat, projects into the circular portion of the opening, and
   B) in the second position no portion of the retainer having a diameter larger than the width of the throat projects into the circular portion of the opening.

10. The assembly of claim 8 wherein:
the platform includes upper and lower surfaces defining an interplanar envelope, and
   A) in the first position the retainer projects into the interplanar envelope and is radially between the pole and the perimeter of the circular portion, and
   B) in the second position the retainer does not project into the interplanar envelope.

11. The assembly of claim 10 wherein when the retainer is in the first position the dimension of the post longitudinally within the interplanar envelope is a first dimension that renders the post incapable of transiting horizontally through the throat and when the retainer is in the second position the dimension of the post longitudinally within the interplanar envelope is a second dimension that renders the post capable of transiting horizontally through the throat and past the edge of the platform.

12. The assembly of claim 8 wherein the retainer is spring biased to the first position.

13. The assembly of claim 8 including a spring radially intermediate the retainer and the pole and in which the spring biases the retainer to the first position.

14. A surgical assembly comprising:
a post having a longitudinally extending axis, the post comprising a pole and a retainer;
a support for resisting movement of the pole in a negative longitudinal direction;
a platform offset from the support in a positive longitudinal direction, the platform having an opening comprised of a circular portion through which the post projects and a throat that extends from the circular portion to an edge of the platform; wherein:
the retainer circumscribes the pole and is longitudinally slidable along the pole to:
   A) a first position in which a first portion of the retainer, which first portion has a diameter larger than the width of the throat, projects into the circular portion of the opening, and
   B) a second position in which no portion of the retainer having a diameter larger than the width of the throat projects into the circular portion of the opening.

15. The surgical assembly of claim 14 wherein the retainer in the first position renders the post incapable of passing through the throat and the retainer in the second position renders the post capable of passing through the throat.

16. The assembly of claim 14 wherein with the retainer in the second position the pole is able to pass through the throat in response to rotation of the post about a laterally extending axis.

17. The assembly of claim 14 wherein:
the platform includes upper and lower surfaces defining an interplanar envelope, and
   A) in the first position the retainer projects into the interplanar envelope and is radially between the pole and the perimeter of the circular portion, and
   B) in the second position the retainer does not project into the interplanar envelope.

18. A surgical assembly comprising:
a support;
a platform offset from the support in a positive longitudinal direction, the platform having an opening comprised of a circular portion and a throat that extends from the circular portion to an edge of the platform; and:
a post having a longitudinally extending axis, the post comprising a pole and a retainer which circumscribes the pole and is longitudinally slidable along the pole to a first position and a second position, the post being positionable on the support so that the post extends longitudinally through the circular portion of the opening and so that when so positioned and with the retainer in the first position, a first portion of the retainer, which has a diameter larger than the width of the throat, projects into the circular portion of the opening and so that when so positioned and with the retainer in the second position no portion of the retainer having a diameter larger than the width of the throat projects into the circular portion of the opening.

* * * * *